(12) United States Patent
Hoover

(10) Patent No.: US 9,751,674 B1
(45) Date of Patent: Sep. 5, 2017

(54) BANDAGE DISPENSER

(76) Inventor: Robert L. Hoover, St. Cloud, MN (US)

( * ) Notice: Subject to any disclaimer, the term of this patent is extended or adjusted under 35 U.S.C. 154(b) by 1450 days.

(21) Appl. No.: 13/213,056

(22) Filed: Aug. 18, 2011

Related U.S. Application Data

(60) Provisional application No. 61/458,857, filed on Dec. 3, 2010.

(51) Int. Cl.
*B65D 83/08* (2006.01)
*B65D 27/08* (2006.01)
*B65D 75/32* (2006.01)
*A61F 13/02* (2006.01)
*A61F 15/00* (2006.01)

(52) U.S. Cl.
CPC ........ *B65D 75/327* (2013.01); *A61F 13/0203* (2013.01); *A61F 15/002* (2013.01); *Y10S 206/82* (2013.01)

(58) Field of Classification Search
CPC .. A61F 13/0203; A61F 15/002; A61F 15/001; Y10S 206/82; B65D 75/327
USPC ......... 206/440–441; 602/57, 41, 43; 211/113
See application file for complete search history.

(56) References Cited

U.S. PATENT DOCUMENTS

| 2,133,609 A | | 10/1938 | Eustis | |
|---|---|---|---|---|
| 2,965,223 A | | 12/1960 | Schladermundt et al. | |
| 3,520,403 A | * | 7/1970 | Moshel | 206/441 |
| 4,666,040 A | * | 5/1987 | Murata | 206/441 |
| 5,366,777 A | * | 11/1994 | Bown et al. | 428/43 |
| 5,511,689 A | | 4/1996 | Frank | |
| 6,079,190 A | | 6/2000 | Simpson | |
| 6,140,549 A | * | 10/2000 | Pompei, Jr. | 602/57 |
| 6,225,522 B1 | * | 5/2001 | Schroeder | 602/57 |
| 7,521,586 B2 | * | 4/2009 | Schroeder | 602/57 |
| 2009/0261010 A1 | * | 10/2009 | Grossman | 206/441 |

* cited by examiner

*Primary Examiner* — Chun Cheung
(74) *Attorney, Agent, or Firm* — Albert W. Watkins

(57) ABSTRACT

A bandage dispenser has a mounting strip onto which are mounted a plurality of partially overlapping bandages. Each bandage is individually wrapped, and the wrapper has a bifurcated opening, with one half of the bifurcated opening bonded to the mounting strip and the second half of the bifurcated opening folded away from the mounting strip to facilitate manual grasping. A person operatively one-handedly grasps the second half of the bifurcated opening, pulls away from the mounting strip to release the sterile bandage, and then may release the bifurcated opening and grasp the sterile bandage. Once the bandage has been applied, a person will finish tearing the bandage wrapper from the mounting strip, revealing the next bandage wrapper bifurcated opening.

2 Claims, 3 Drawing Sheets

BANDAGE DISPENSER

CROSS REFERENCE TO RELATED APPLICATIONS

This application claims the benefit of U.S. provisional patent application 61/458,857, filed on Dec. 3, 2010, and having the same title and inventorship, the contents which are incorporated herein by reference in entirety.

BACKGROUND OF THE INVENTION

1. Field of the Invention

The present invention pertains generally to special receptacles or packages for body treatment articles, and more particularly to a package displaying a plurality of individually prepackaged adhesive bandages that may individually be removed and unwrapped with a one-hand single motion.

2. Description of the Related Art

Bandages have likely been used since before recorded history, and have also undoubtedly been fashioned from many different materials. However, since the popular identification of micro-organisms by the likes of Louis Pasteur, there has been an ever-increasing awareness, albeit gradually, in the medical field of the importance of sterility in the care and treatment of wounds. For a time in relatively recent history, more and better antibiotics and cleansers were developed that facilitated the creation of a sterile environment, even without a wound being perfectly clean or a bandage being sterile. However, particularly recently there have been several bacteria that have developed resistance to most or even all of the known antibiotic treatments. Consequently, health care professionals today cannot rely solely on antibiotics. With every passing day, the importance of a sterile treatment environment, sterile wound cleansing, and sterile bandages increases.

One benefit of this recognition has been the improved packaging of bandages, so that most modern bandages are produced in a sterile environment and are individually wrapped to protect and preserve each bandage. Very commonly, individually wrapped sterile bandages may also be provided with adhesive tape, and are popularly sold, for example, under the Band-Aids™ brand. These individually wrapped sterile bandages are produced and then further packaged in a paperboard box or a metal container, both of which will typically use a hinged closure flap to fully enclose and protect the individually wrapped sterile bandages during storage.

The retrieval of bandages from storage is always fraught with challenges. When the need for a bandage arises, first the container of bandages must be located and retrieved from storage and opened. There are many different styles of bandages, and the contents of a particular paperboard or metal container is generally not clear or certain until the container is opened. Much inconvenience arises when the container is opened, only for the person to discover that the supply of bandages needed to treat a particular wound have already been exhausted and not restocked. Furthermore, the opening of the container in many cases requires or is greatly facilitated by the use of two hands.

In the event of good fortune, where a properly sized individually wrapped sterile bandage is located, then the subsequent application and use of the individual bandage presents further challenge. First, the bandage must be separated from the individual wrapper. Many bandages today have a bifurcated end on the bandage wrapper, where the top and bottom sheets that together form the bandage wrapper are separated. A person will grasp each sheet separately, with one sheet in each hand, and then pull the two sheets apart to reveal the bandage enclosed therein. Once again, this requires or is greatly facilitated by the use of two hands.

Since there are several steps that require the use of two hands, a person who is wounded may often times be unable to access an individual bandage. Likewise, in a health care facility, a health-care provider such as a doctor or nurse may have only one hand available, and so again at those times will be unable to access an individual bandage. Instead, the health care provider will have to request and wait for another provider to assist.

Others have developed a variety of bandage dispensers to try to improve upon the existing paperboard box or metal containers. Exemplary patents, the teachings and contents which are incorporated herein by reference, include U.S. Pat. No. 2,133,609 by Eustis, entitled "Surgical dressing"; U.S. Pat. No. 2,965,223 by Schladermundt et al, entitled "Dispenser pack of individual adhesive bandages"; U.S. Pat. No. 5,511,689 by Frank, entitled "Dispensing device for adhesive-backed articles"; and U.S. Pat. No. 6,079,190 by Simpson, entitled "Bandage package and method of dispensing". While these patents offer significant improvement over the prior art containers, and offer high density packaging of bandages, none offer a preferred combination of one-handed manual access and opening of individual wrappers, visual assessment of supply stock from a distance; and a sterile individual wrapper.

In addition to the aforementioned patents, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a bandage dispenser, having a generally planar bandage dispenser substrate and at least one row of partially overlapping individually wrapped sterile bandages mounted onto a dispensing region within the generally planar bandage dispenser substrate. Each one of the individually wrapped sterile bandages are bifurcated at one end and have a first sheet defining a top portion of the wrapper, and a second sheet defining the opposed bottom portion of the wrapper. A bond adheres a one of the first and second sheets to the generally planar bandage dispenser substrate.

OBJECTS OF THE INVENTION

Exemplary embodiments of the present invention solve inadequacies of the prior art by providing a generally planar bandage dispenser having at least one row of partially overlapping individually wrapped sterile bandages. Each of the individually wrapped sterile bandages are adhered on one surface of a bifurcated wrapper to the generally planar bandage dispenser.

A first object of the invention is to package a plurality of individually packaged sterile bandages into a single display unit. A second object of the invention is to enable a person to visually determine the quantity of sterile bandages instantaneously at a significant distance from the single display unit. Another object of the present invention is to facilitate the removal of individual bandages from their individual sterile packages using only a single hand, without any risk to the sterility of the bandage being removed. A further object of the invention is to provide a high density display unit displaying many individually packaged sterile bandages in a small space. Yet another object of the present invention is to enable the single display unit to be populated with individually packaged sterile bandages immediately subsequent to the production and packaging of individually packaged sterile bandages, preferably in a way that permits automation of the populating. Another object of the invention is the provision of a low-cost single display unit. A further object of the invention is for the use of the single display unit to be intuitive, and so be immediately used by most persons without consequential training being required.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

Figure 6:
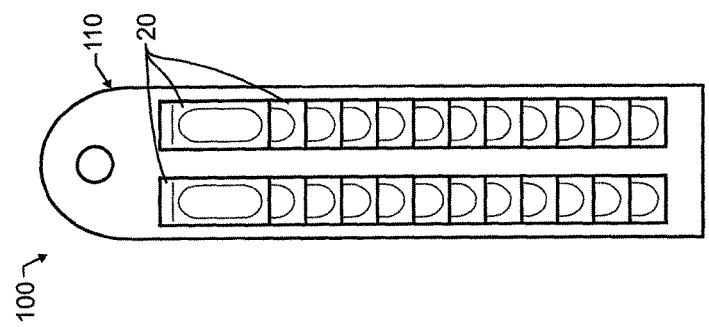
FIG. 6 illustrates an alternative embodiment bandage dispense designed in accord with the teachings of the present invention from a front plan view.
Figure 2:
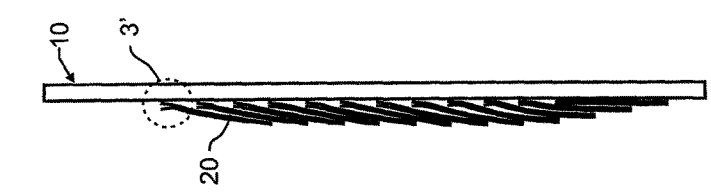
FIG. 2 illustrates the preferred embodiment bandage dispenser of FIG. 1 from a side plan view.

Bandage dispenser 1 is illustrated for exemplary purposes in FIGS. 1-5, and includes a generally planar bandage dispenser substrate 10. At least one row of partially overlapping individually wrapped sterile bandages 20 are mounted onto a dispensing region 12. An optional mounting region 14 in the preferred embodiment bandage dispenser 1 is provided with a hanging hole 16 suitable for hanging from a nail or other protrusion extending from a surface. Other mounting structures besides or in addition to hanging hole 16 are further contemplated herein, and may include, for exemplary purposes only and not limiting solely thereto, magnets, hook-and-loop fasteners such as Velcro™, temporary or permanent adhesives, and any other suitable apparatus or fasteners known in the fastener and mounting arts. These mounting structures or fasteners may be provided in optional mounting region 14, or may alternatively be coatings or backings provided on a major surface of generally planar bandage dispenser substrate 10 opposed to the major surface to which individually wrapped sterile bandages 20 are mounted.

Substrate 10 in the preferred embodiment is fabricated from plastic sheet that is pliable, but which has sufficient rigidity to resist substantial deformation when an individually wrapped sterile bandage 20 is opened one-handedly. Nevertheless, any suitable material may be selected, depending upon the needs of a designer and price and availability of material. Exemplary alternative materials include wood, cardboard, paperboard, paper, laminates, composites or any other suitable materials.

Figure 1:
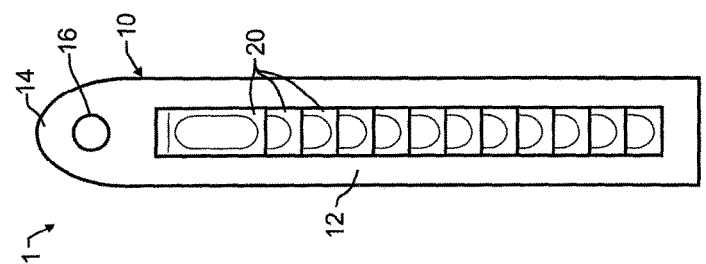
FIG. 1 illustrates a preferred embodiment bandage dispenser designed in accord with the teachings of the present invention from a front plan view.

Most preferably, individually wrapped sterile bandages 20 overlap partially but not completely with adjacent individually wrapped sterile bandages 20 to increase the density of available bandages. Because bandages 20 do not totally overlap with each other, and instead only partially overlap, then based upon the total extent of overlapped bandages 20, such as the vertical extent of bandages 20 as illustrated in FIG. 1, a person can reasonably visually discern from a significant distance beyond arm's reach approximately how many bandages remain.

Figure 3:
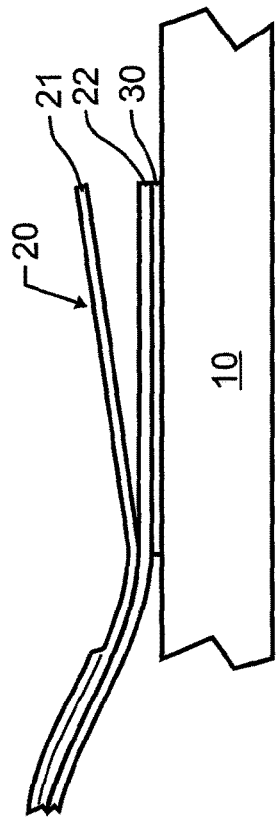
FIG. 3 illustrates a side sectional view of the preferred embodiment bandage dispenser of FIG. 2 taken along line 3'.
Figure 4:
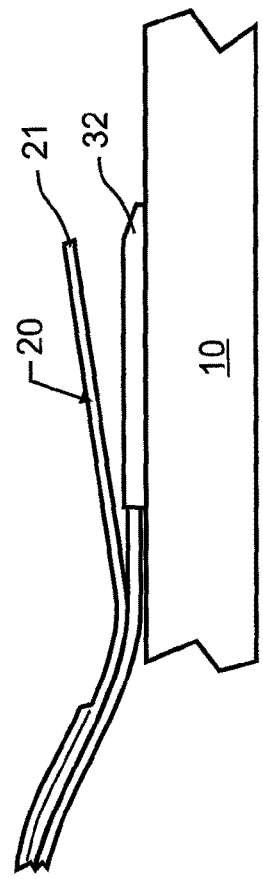
FIG. 4 illustrates a side sectional view of a first alternative embodiment bandage dispenser from the same view as that of FIG. 3.

Individually wrapped sterile bandages 20 will most preferably be bifurcated at one end, as is commonly known in the adhesive bandage art and illustrated herein in FIGS. 3 and 4. A first sheet 21 may serve as a top portion of the wrapper, and a second sheet 22 may define the opposed bottom portion of the wrapper, where the references to top and bottom are understood to be interchangeable. As illustrated in FIG. 3, second sheet 22 is preferably adhered to generally planar bandage dispenser substrate 10 through a bond 30. Bond 30 may be formed from an adhesive, such as a Pressure-Sensitive Acrylic (PSA), a moisture sensitive adhesive, various cements, thermally activated or Ultra-Violet (UV) cured adhesives, or any other adhesive or alternative to an adhesive. The adhesive is not critical to the present invention, and may comprise an adhesive applied to either second sheet 22 or to generally planar bandage dispenser substrate 10 prior to attachment therebetween. Further, the particular technique for applying the adhesive is not critical to the present invention, and so for exemplary purposes only, may include such techniques as roll or contact applicators, screen printing, spraying, ink jet or thermal transfer, or any other suitable technique. Alternatives to adhesives include, for exemplary purposes only and not limiting solely thereto, such techniques as thermal bonding, friction welding or ultrasonic welding, either directly between second sheet 22 and generally planar bandage dispenser substrate 10, or through some intermediate layer that may provide desired bonding characteristics, processes or handling.

FIG. 4 illustrates another alternative embodiment, using the same numbering as found in FIG. 3, but instead of bond 30, a tape 32 may be applied over second sheet 22, thereby securing second sheet 22 to substrate 10. As illustrated in FIG. 4, and if so desired, tape 32 may be applied over bifurcated end 22, and may or may not wrap from a front major surface of generally planar bandage dispenser substrate 10 to a minor surface or to the back major surface, depending upon the wishes and needs of a designer.

Figure 5:
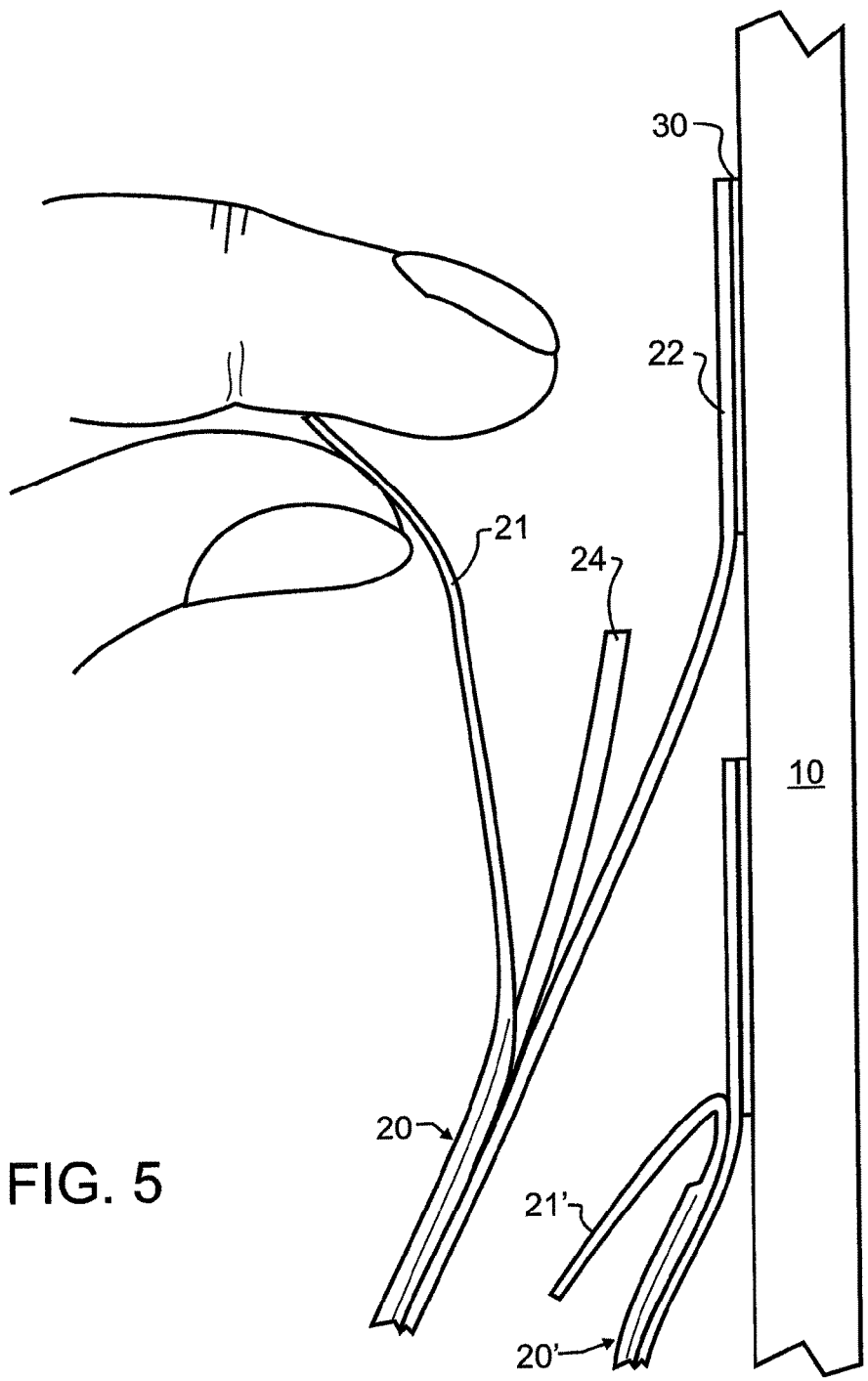
FIG. 5 illustrates the preferred embodiment bandage dispenser of FIG. 1 from an enlarged side section view similar to that of FIG. 3, but illustrating two overlapping bandages and illustrating the partial removal of one of the bandages.

As illustrated in FIG. 5, each of the individually wrapped sterile bandages 20 are adhered on one surface of a bifurcated wrapper end 22 to the generally planar bandage dispenser substrate 10. While in the prior art this bifurcated wrapping is designed to be grasped with one hand at each one of bifurcated wrapper ends 21, 22, owing to bond 30 or the equivalent, a person may simply grasp a single wrapper end with a single hand, such as end 21 as illustrated in FIG. 5, and then peel bifurcated wrapper end 21 down and away from bifurcated end 22, thereby further separating top layer 21 from bottom layer 22 and releasing bandage 24, which may be an adhesive bandage or bandage without adhesive, from bifurcated wrapper ends 21, 22. Once sufficiently released, bandage 24 may then be grasped with the same hand that separated top layer 21 from bottom layer 22, and then subsequently applied to a patient.

In the preferred embodiment illustrated in FIG. 5, when uppermost individually wrapped sterile bandage 20 is opened and bandage 24 removed therefrom, then bifurcated end 22 may preferably be forcibly detached from substrate 10. As may be apparent, substrate 10 will most preferably be sufficiently more durable than at least one of bifurcated end 22 or bond 30 that any failure occurs only in either bifurcated end 22 or bond 30, thereby only separating uppermost individually wrapped sterile bandage 20 from substrate 10. Once uppermost individually wrapped sterile bandage 20 has been separated, individually wrapped sterile bandage 20' becomes the new uppermost individually wrapped sterile bandage. To better facilitate manual grasping, in the preferred embodiment illustrated in FIG. 5, at least the second and subsequent individually wrapped sterile bandages 20' may also have the bifurcated end 21' that is not attached to substrate 10 folded downward and outward from substrate 10.

FIG. 6 simply illustrates that the particular geometry of substrate 10 is not critical to the present invention, and so a plurality of rows of partially overlapped individually wrapped sterile bandages 20 may be provided.

A secondary covering, such as a clear plastic sheet bonded at a top near to but below hanging hole 16, and hanging down therefrom, may optionally be provided to gain additional protection against accidental or unintentional spraying or other contamination of individually wrapped sterile bandages 20. A person accessing individually wrapped sterile bandages 20 would slide their hand under the secondary covering and lift to access an individually packaged sterile bandage.

Since in the preferred and alternative embodiments illustrated in the Figures and described herein each bond 30 is at a predictable and repeatable spacing from the next previous bond, each bond and each individually wrapped sterile bandage 20 may be placed or formed using automated assembly equipment. Consequently, preferred embodiment bandage dispenser 1 may be produced by populating generally planar bandage dispenser substrate 10 with individually wrapped sterile bandages 20 immediately subsequent to the production and packaging of individually packaged sterile bandages 20, preferably in a way that permits automation of the populating. The resulting bandage dispenser 1 is a low-cost display unit that is intuitive to use by most persons without consequential training.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:

1. A bandage dispenser, comprising:
   a generally planar bandage dispenser substrate;
   at least one row of partially overlapping individually wrapped sterile bandages mounted onto a dispensing region within said generally planar bandage dispenser substrate, each one of said individually wrapped sterile bandages bifurcated at one end and having a first sheet defining a top portion of the wrapper, and a second sheet defining the opposed bottom portion of the wrapper; and
   each one of said partially overlapping individual wrapped sterile bandages second sheets adjacent to said bifurcated end adhered to said generally planar bandage dispenser substrate;
   an uppermost one of said partially overlapping individually wrapped sterile bandages bifurcated end exposed; and
   each one of said partially overlapping individually wrapped sterile bandages bifurcated ends subsequent to said uppermost one concealed between a next adjacent and relatively more upper one of said partially overlapping individually wrapped sterile bandages and said generally planar bandage dispenser substrate;
   a secondary covering bonded above said partially overlapping individually wrapped sterile bandages and covering a plurality of said partially overlapping individually wrapped sterile bandages while remaining manually repeatably liftable therefrom.

2. The bandage dispenser of claim 1, wherein said secondary covering further comprises a transparent plastic sheet.

* * * * *